(12) United States Patent
Muller et al.

(10) Patent No.: US 11,331,038 B2
(45) Date of Patent: May 17, 2022

(54) APPARATUS FOR DETERMINING A PROPERTY OF A TISSUE

(71) Applicant: KONINKLIJKE PHILIPS N.V., Eindhoven (NL)

(72) Inventors: Manfred Muller, Eindhoven (NL); Gerhardus Wilhelmus Lucassen, Eindhoven (NL); Christian Reich, Eindhoven (NL); Payal Keswarpu, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1398 days.

(21) Appl. No.: 14/378,800

(22) PCT Filed: Mar. 1, 2013

(86) PCT No.: PCT/IB2013/051652
§ 371 (c)(1),
(2) Date: Aug. 14, 2014

(87) PCT Pub. No.: WO2013/132400
PCT Pub. Date: Sep. 12, 2013

(65) Prior Publication Data
US 2016/0038076 A1 Feb. 11, 2016

Related U.S. Application Data

(60) Provisional application No. 61/608,173, filed on Mar. 8, 2012.

(51) Int. Cl.
*A61B 5/00* (2006.01)
*A61B 5/145* (2006.01)
*A61B 5/1455* (2006.01)

(52) U.S. Cl.
CPC ............ *A61B 5/444* (2013.01); *A61B 5/0084* (2013.01); *A61B 5/14546* (2013.01);
(Continued)

(58) Field of Classification Search
CPC .................................................. A61B 5/0059
See application file for complete search history.

(56) References Cited

U.S. PATENT DOCUMENTS 5,713,364 A * 2/1998 DeBaryshe ........ A61B 1/00059
250/461.2
5,746,210 A * 5/1998 Benaron .............. A61B 5/0075
356/338

(Continued)

FOREIGN PATENT DOCUMENTS

EP 0843986 A2 5/1998
JP 2002535645 A 10/2002

(Continued)

OTHER PUBLICATIONS

"Depth-cumulated epithelial redox ratio and stromal collagen quantity as quantitative intrinsic indicators for differentiating normal, inflammatory, and dysplastic epithelial tissues" by Zhou et al., Applied Physics Letters, vol. 97, 2010.*

(Continued)

*Primary Examiner* — Michael R Bloch

(57) ABSTRACT

The invention relates to an apparatus for determining a property of a tissue, particularly cancer of cervical tissue. A light providing unit (7, 8, 9) provides light for illuminating the tissue (6) and a light detection unit (10) detects light from the tissue, wherein a first signal being indicative of light (11) having been influenced by an epithelium region (R1), a second signal being indicative of light (12) having been influenced by a boundary region (R2) and a third signal being indicative of light (13) having been influenced by a stroma region (R3) are generated, and wherein a tissue (Continued)

property is determined based on the first, second and third signals. This allows for an determination of a tissue property, which is based on a combination of optical properties measured in the three different regions, resulting in an improved determination of the tissue property, in particular in improved cancer detection.

15 Claims, 5 Drawing Sheets

(52) U.S. Cl.
    CPC .......... *A61B 5/14551* (2013.01); *A61B 5/443* (2013.01); *A61B 5/4872* (2013.01); *A61B 5/7278* (2013.01); *A61B 5/7282* (2013.01); *A61B 2562/0238* (2013.01); *A61B 2562/0242* (2013.01); *A61B 2576/00* (2013.01)

(56) References Cited

U.S. PATENT DOCUMENTS

| | | | |
|---|---|---|---|
| 6,258,044 | B1 | 7/2001 | Lonky et al. |
| 6,990,369 | B2 | 1/2006 | Ganjbaklche |
| 7,202,947 | B2 | 4/2007 | Liu |
| 2003/0060692 | A1 | 3/2003 | Ruchti |
| 2005/0143663 | A1* | 6/2005 | Liu .................. A61B 5/0059 600/476 |
| 2012/0080616 | A1* | 4/2012 | Schoenborn ......... A61B 5/0059 250/459.1 |
| 2013/0017200 | A1 | 1/2013 | Scheer et al. |

FOREIGN PATENT DOCUMENTS

| | | |
|---|---|---|
| JP | 2004041815 A | 10/2002 |
| JP | 2004337625 A | 2/2004 |
| JP | 2004337625 A | 12/2004 |
| WO | WO2007006039 A2 | 1/2007 |

OTHER PUBLICATIONS

"A model of FAS1 domain 4 of the corneal protein βig-h3 gives clearer view on corneal dystrophies" by Clout et al., Molecular Vision, V.9, pp. 440-448, 2003.*

An anatomy digital library, Atlas of Microscopic Anatomy, Section 7 by Bergman et al., 2006.*

Zhuo Shuangmu et al: "Depth-Cumulated Epithelial Redox Ratio and Stromal Collagen Quantity as Quantitative Intrinsic Indicators for Differentiating Normal, Inflammatory, and Dysplastic Epithelial Tissues", Applied Physics Letters, AIP, American Institute of Physics, Melville, NY, US, vol. 97, No. 17, Oct. 25, 2010, pp. 173701-173701, XP012137473.

Nachabe R. et al., "Estimation of Lipid and Water Concentrations in Scattering Media with Diffuse Optical Spectroscopy from 900 to 1600 nm" Journal of Biomedical Optics, vol. 15, No. 3, (2010).

Brynolf M. et al., "Optical Detection of the Brachial Plexus for Peripheral Nerve Blocks", Regional Anesthesia and Pain Medicine, vol. 36, No. 4, pp. 350-357, (2011).

Zhu C. et al., "Model Based and Empirical Spectral Analysis for the Diagnosis of Breast Cancer", Optics Express, vol. 16, No. 19, p. 14961-14978, (2008).

Skala M.C. et al., "An Investigation of Fiber-Optic Probe Designs for Optical Spectroscopic Diagnosis of Epithelial Pre-Cancers", Lasers in Surgery and Medicine, vol. 34, No. 1, pp. 25-38, (2004).

Schwarz R.A. et al., "Ball Lens Coupled Fiber-Optic Probe for Depth-Resolved Spectroscopy of Epithelial Tissue", 2005 Optical Society of America, May 15, 2005, vol. 30, No. 10, Optics Letters, pp. 1159-1161.

* cited by examiner

APPARATUS FOR DETERMINING A PROPERTY OF A TISSUE

CROSS-REFERENCE TO PRIOR APPLICATIONS

This application is the U.S. National Phase application under 35 U.S.C. § 371 of International Application Serial No. PCT/IB2013/051652, filed on Mar. 1, 2013, which claims the benefit of U.S. Application Ser. No. 61/608,173, filed on Mar. 8, 2012. These applications are hereby incorporated by reference herein.

FIELD OF THE INVENTION

The invention relates to an apparatus, a method and a computer program for determining a property of a tissue. The invention relates further to an optical measurement device and a tissue property determination device for determining a property of a tissue.

BACKGROUND OF THE INVENTION

U.S. Pat. No. 7,202,947 B2 discloses a fluorescence instrument comprising a light source for producing light and illumination means for conveying the light to the surface of a subject to be examined such that the light may be applied to the surface of the subject at a plurality of incidence angles. The fluorescence instrument further comprises collection means for collecting light emanating from the surface of the subject which is produced by fluorescence within the subject and beneath the surface, and a detector for measuring the collected light. A means for changing the incidence angle is used to enable a series of fluorescence measurements of the subject to be made, at different depths beneath the surface, wherein the fluorescence measurement results are used for determining tissue properties.

This determination of tissue properties can only be performed, if the tissue emits fluorescence light in a sufficiently large amount, and does not yield very accurate results.

SUMMARY OF THE INVENTION

It is an object of the present invention to provide an apparatus, a method and a computer program for determining a property of a tissue, wherein the property of the tissue can be determined with increased accuracy. It is a further object of the present invention to provide an optical measurement device and a tissue property determination device, which can be used for determining the property of the tissue more accurately.

In a first aspect of the present invention an apparatus for determining a property of a tissue is provided, wherein the tissue comprises epithelium and stroma and wherein the apparatus comprises:

an optical measurement device with a light providing unit for providing light for illuminating the tissue and a light detection unit for detecting light from the tissue, wherein the light providing unit and the light detection unit are adapted to generate a first signal being indicative of light having been influenced by an epithelium region of the tissue comprising the epithelium, a second signal being indicative of light having been influenced by a boundary region of the tissue comprising a boundary between the epithelium and the stroma and a third signal being indicative of light having been influenced by a stroma region of the tissue comprising the stroma, and a tissue property determination device for determining a tissue property based on the first, second and third signals.

Since the first signal is indicative of light having been influenced by the epithelium region, the second signal is indicative of light having been influenced by the boundary region between the epithelium region and the stroma region, the third signal is indicative of light having been influenced by the stroma region and the tissue property is determined based on these first, second and third signals, optical properties measured in the three different regions, can be used in a combined way for determining the tissue property, which leads to an improved determination of the tissue property.

The light having been influenced by the epithelium region, which is used for generating the first signal, has preferentially only traversed the epithelium of the tissue before being detected. The light having been influenced by the stroma region, which is used for generating the third signal, has preferentially mainly traversed the stroma of the tissue and, for reaching the stroma from the outside of the tissue, less traversed the epithelium of the tissue before being detected by the light detection unit. The light having been influenced by the boundary region, which is used for generating the second signal, preferentially traverses an area of the tissue before being detected, which is substantially located between the areas that have been traversed by the light used for generating the first and third signals.

The light detected from the tissue by the light detection unit is preferentially the light, which has been provided for illuminating the tissue, after the light has been influenced by the tissue, for instance, after the light has been reflected, absorbed and/or scattered by the tissue.

The tissue is preferentially cervical tissue.

It is preferred that the light providing unit and the light detection unit are adapted such that the generated first signal is indicative of light having an average penetration depth in the tissue being smaller than 0.5 mm, the generated second signal is indicative of light having an average penetration depth in the tissue being larger than 0.2 mm and smaller than 0.75 mm, and the generated third signal is indicative of light having an average penetration depth in the tissue being larger than 0.5 mm. If the first signal is indicative of light having an average penetration depth being smaller than 0.5 mm, if the second signal is indicative of light having an average penetration depth being larger than 0.2 mm and smaller than 0.75 mm and if the generated third signal is indicative of light having an average penetration depth being larger than 0.5 mm, the first signal is indicative of the epithelium region, the second signal is indicative of the boundary region and the third signal is indicative of the stroma region in a way which further increases the accuracy of determining the tissue property, in particular if the tissue is cervical tissue.

Light, which is detected by the light detection unit for generating a certain signal, may have penetrated the tissue up to different penetration depths in the tissue. For instance, different parts of the light like different light beams or different photons may have penetrated the tissue up to different penetration depths. The average penetration depth is preferentially defined as being the average of these different penetration depths, wherein the average may be the median or a weighted average, wherein each of the different penetration depths is weighted with the respective light intensity or the respective number of photons.

It is further preferred that the optical measurement device is adapted such that the generated signals are spectra, wherein the tissue property determination device is adapted to determine the tissue property based on a first spectrum being the first signal, a second spectrum being the second signal and a third spectrum being a third signal. The light providing unit and the light detection unit are preferentially adapted to perform a diffuse reflectance spectrometry for generating three diffuse reflectance spectra being the first, second and third signals, wherein the tissue is illuminated by white light. However, also other spectra can be measured like fluorescence spectra or Raman spectra. If the determination of the tissue property is based on first, second and third signals, which are indicative of the epithelium region, the boundary region and the stroma region and which are spectra, the accuracy of determining the tissue property can be further increased.

It is also preferred that the optical measurement device is adapted to a) generate several first signals being indicative of light having been influenced by the epithelium region, wherein different first signals are indicative of light within different wavelength ranges, b) generate several second signals being indicative of light having been influenced by the boundary region, wherein different second signals are indicative of light within different wavelength ranges, and c) generate several third signals being indicative of light having been influenced by the stroma region, wherein different third signals are indicative of light within different wavelength ranges, wherein the tissue property determination device is adapted to determine the tissue property based on the several first, second and third signals. For instance, a first set of first, second and third signals can be determined in a first wavelength range and a second set of first, second and third signals can be generated in a second wavelength range. The first wavelength range is, for example, a visible wavelength range and the second wavelength range is, for example, an infrared wavelength range. Thus, in an embodiment a first set of first, second and third signals can be generated based on light having been influenced by the tissue, in particular having been scattered back by the tissue, in the visible wavelength range and a second set of first, second and third signals can be generated based on light influenced by the tissue, in particular scattered back by the tissue, in the infrared spectral region. If the tissue property determination device determines the tissue property not only based on a single set of first, second and third signals, but on two or more sets of first, second and third signals, which correspond to different wavelengths, the accuracy of determining the tissue property can be further improved.

In a preferred embodiment the light providing unit is adapted to provide one or several illumination locations from which one or several light beams emanate in one or several illumination directions, wherein the light detection unit is adapted to provide one or several detection locations at which light is detected, wherein the light providing unit and the light detection unit are adapted to provide three combinations of an illumination location and a detection location and to generate the first signal depending on the light emanating from an illumination location and being detected by a detection location of a first combination, the second signal depending on the light emanating from an illumination location and being detected by a detection location of a second combination, and the third signal depending on the light emanating from an illumination location and being detected by a detection location of a third combination. In particular, the optical measurement device can comprise a measurement head with an outer plane abutting surface for being abutted to the tissue, while illuminating the tissue with light and detecting light from the tissue, wherein the illumination and detection directions are perpendicular to the abutting surface, wherein the distance between the illumination location and the detection location of the first combination is smaller than 0.6 mm, the distance between the illumination location and the detection location of the second combination is between 0.6 mm and 1.2 mm and the distance between the illumination location and the detection location of the third combination is between 1.2 mm and 3.0 mm. In a preferred embodiment the distance between the illumination location and the detection location of the first combination is 0.3 mm, the distance between the illumination location and the detection location of the second combination is 1.0 mm and the distance between the illumination location and the detection location of the third combination is 1.5 mm. This allows optically sensing the epithelium region, the boundary region and the stroma region in a relatively simple way by just positioning the one or several illumination locations and the one or several detection locations such that the respective light traverses the desired respective region.

The light providing unit preferentially comprises a light emission unit with one or several light sources for generating light and one or several source fibers for guiding the light from the light emission unit to one or several illumination locations. The light detection unit preferentially comprises one or several light detectors, in particular spectrometers, and one or several detection fibers for guiding the light received from the tissue at one or several detection locations to the one or several light detectors.

In an embodiment the light providing unit is adapted to provide a first light beam for illuminating the tissue at a first illumination location in a first illumination direction, a second light beam for illuminating the tissue at a second illumination location in a second illumination direction and a third light beam for illuminating the tissue at a third illumination location in a third illumination direction, wherein the light detection unit is adapted to detect the light from the tissue at a first detection location in a first detection direction, wherein the distances from the illumination locations to the first detection location and the illumination and detection directions are adapted such that the part of the first light beam, which is detected at the first detection location, traverses the epithelium region for generating the first signal, the part of the second light beam, which is detected at the first detection location, traverses the boundary region for generating the second signal and the part of the third light beam, which is detected at the first detection location, traverses the stroma region for generating the third signal. In addition, the light detection unit can be adapted to detect the light from the tissue at a second detection location in a second detection direction, wherein the distances from the illumination locations to the second detection location and the illumination and detection directions are adapted such that the part of the first light beam, which is detected at the second detection location, traverses the epithelium region for generating a further first signal, the part of the second light beam, which is detected at the second detection location, traverses the boundary region for generating a further second signal and the part of the third light beam, which is detected at the second detection location, traverses the stroma region for generating a further third signal, wherein the light detection unit is adapted to detect at the first detection location light within a first wavelength range and at the second detection location light within a second wavelength range, in order to generate two sets of first, second and third signals for two different wavelength ranges, wherein the tissue property determination device is adapted to determine the property of the tissue based on the two sets of signals. The first wavelength range is preferentially within the visible wavelength range and the second wavelength range is preferentially within the infrared wavelength range.

It is also preferred that the tissue property determination device is adapted to perform at least one of a feature extraction technique, a fitting to an analytical model and a multivariate analysis technique for determining the tissue property. Moreover, the tissue property determination device can be adapted to determine as an intermediate property at least one of blood fraction, blood saturation, water content, lipid content, carotene concentration, elastin concentration, collagen concentration, nicotinamide adenine dinucleotide concentration (NADH), flavin adenine dinucleotide (FAD) concentration, porphyrin concentration, vitamin concentration in at least one of the epithelium region, the boundary region and the stroma region, and to determine the tissue property depending on the determined intermediate property. For instance, at least one of a feature extraction technique, a fitting to an analytical model and a multivariate analysis technique can be applied to the first signal for determining an intermediate property of the epithelium region, to the second signal for determining an intermediate property of the boundary region and to the third signal for determining an intermediate property of the third signal, wherein the intermediate properties determined for the different regions can be used for determining the final tissue property. For determining an intermediate property of the epithelium region several first signals, which correspond to different wavelength ranges, can be used. Also for determining an intermediate property of the boundary region and of the stroma region, respectively, several second signals and several third signals, respectively, which correspond to different wavelength ranges, can be used.

It is further preferred that the tissue property determination device is adapted to determine at least one of healthy tissue and cancer as the tissue property based on the signals. In particular, the tissue property determination device can be adapted to determine a stage of the cancer as the tissue property. For instance, the tissue property determination device can be adapted to determine whether invasive cancer is present. It is also preferred that the tissue is cervical tissue and the tissue property determination device is adapted to determine cervical intraepithelial neoplasia (CIN) as the tissue property based on the signals. Thus, the tissue property determination device can be adapted to distinguish between healthy tissue, CIN and cancer, in particular invasive cancer. Moreover, it can be adapted to discriminate between different cancer stages and between different grades of CIN, for instance, between CIN1, CIN2 and CIN3. The tissue property determination device can also be adapted to discriminate between squamous and columnar healthy tissue, i.e. ectocervix and endocervix. Moreover, the tissue property determination device can be adapted to recognize non-cancerous pathological tissue, in particular different kinds of non-Cancerous pathological tissue like inflammations or ulcers.

For instance, the blood fraction can be determined as an intermediate property in the epithelium region, the boundary region and the stroma region. The tissue property determination device can be adapted to determine a CIN1 lesion, if the blood fraction is increased in the boundary region, but not or too a lower degree in the stroma region or in the epithelium region. Moreover, the tissue property determination device can be adapted to determine invasive cancer, in particular invasive stroma, if the blood fraction is increased in all three regions. In order to determine whether the blood fraction is increased or decreased, the blood fraction can be compared with predefined thresholds, which preferentially define a region of blood fractions, which can be regarded as being normal. These thresholds can be determined by training blood fraction measurements, which are performed on tissue, which is known to be healthy and which provides therefore a normal blood fraction value, and on tissue, which is known to be non-healthy and which provides therefore increased or decreased blood fraction values.

In a preferred embodiment the tissue property determination device is further adapted to compare the signals with predefined expectations and to generate an error signal, if the signals do not correspond to the predefined expectations. For instance, the tissue property determination device can be adapted to directly compare the signals, i.e. the optical measurements, with the expectations, or the property determination unit can be adapted to process the signals and to compare the processing results with the expectations. The processing can be defined by processing steps, which are performed for determining the tissue property. Thus, if the measurements or the analysis are yielding wrong or inclusive results, an error signal can be generated. This error signal can be an acoustical and/or optical signal, which can be output, in order to indicate the error to a user. The error signal can also be indicative of the kind of error, wherein an output unit like a display can be adapted to show the kind of error to the user based on the error signal. Moreover, the apparatus can be adapted to repeat the measurement and the analysis, if an error signal has been generated, wherein the error signal may not necessarily be output to a user, but may be an internal signal which triggers the repetition of the measurement and the analysis.

In a further aspect of the present invention an optical measurement device for cooperating with a tissue property determination device for determining a property of a tissue is presented, wherein the tissue comprises epithelium and stroma and wherein the optical measurement device comprises a light providing unit for providing light for illuminating the tissue and a light detection unit for detecting light from the tissue, wherein the light providing unit and the light detection unit are adapted to generate a first signal being indicative of light having been influenced by an epithelium region of the tissue comprising the epithelium, a second signal being indicative of light having been influenced by a boundary region of the tissue comprising a boundary between the epithelium and the stroma and a third signal being indicative of light having been influenced by a stroma region of the tissue comprising the stroma.

In a further aspect of the present invention a tissue property determination device for cooperating with an optical measurement device for determining a tissue property is presented, wherein the tissue comprises epithelium and stroma and the optical measurement device comprises a light providing unit for providing light for illuminating the tissue and a light detection unit for detecting light from the tissue, wherein the light providing unit and the light detection unit are adapted to generate a first signal being indicative of light having been influenced by an epithelium region of the tissue comprising the epithelium, a second signal being indicative of light having been influenced by a boundary region of the tissue comprising a boundary between the epithelium and the stroma and a third signal being indicative of light having been influenced by a stroma region of the tissue comprising the stroma, wherein the tissue property determination device is adapted to determine a tissue property based on the first, second and third signals.

In a further aspect of the present invention a method for determining a property of a tissue is presented, wherein the tissue comprises epithelium and stroma and wherein the method comprises:

providing light for illuminating the tissue by a light providing unit of an optical measurement device and detecting light from the tissue by a light detection unit of the optical measurement device, wherein the light providing unit and the light detection unit generate a first signal being indicative of light having been influenced by an epithelium region of the tissue comprising the epithelium, a second signal being indicative of light having been influenced by a boundary region of the tissue comprising a boundary between the epithelium and the stroma and a third signal being indicative of light having been influenced by a stroma region of the tissue comprising the stroma, determining a tissue property based on the first, second and third signals by a tissue property determination device.

In a further aspect of the present invention a computer program for determining a property of a tissue is presented, wherein the tissue comprises epithelium and stroma and wherein the computer program comprises program code means for causing an apparatus to carry out the steps of a method, when the computer program is run on a computer controlling the apparatus.

It shall be understood that the apparatus, the optical measurement device the tissue property determination device, the method for determining a property of a tissue and the computer program of the claims have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
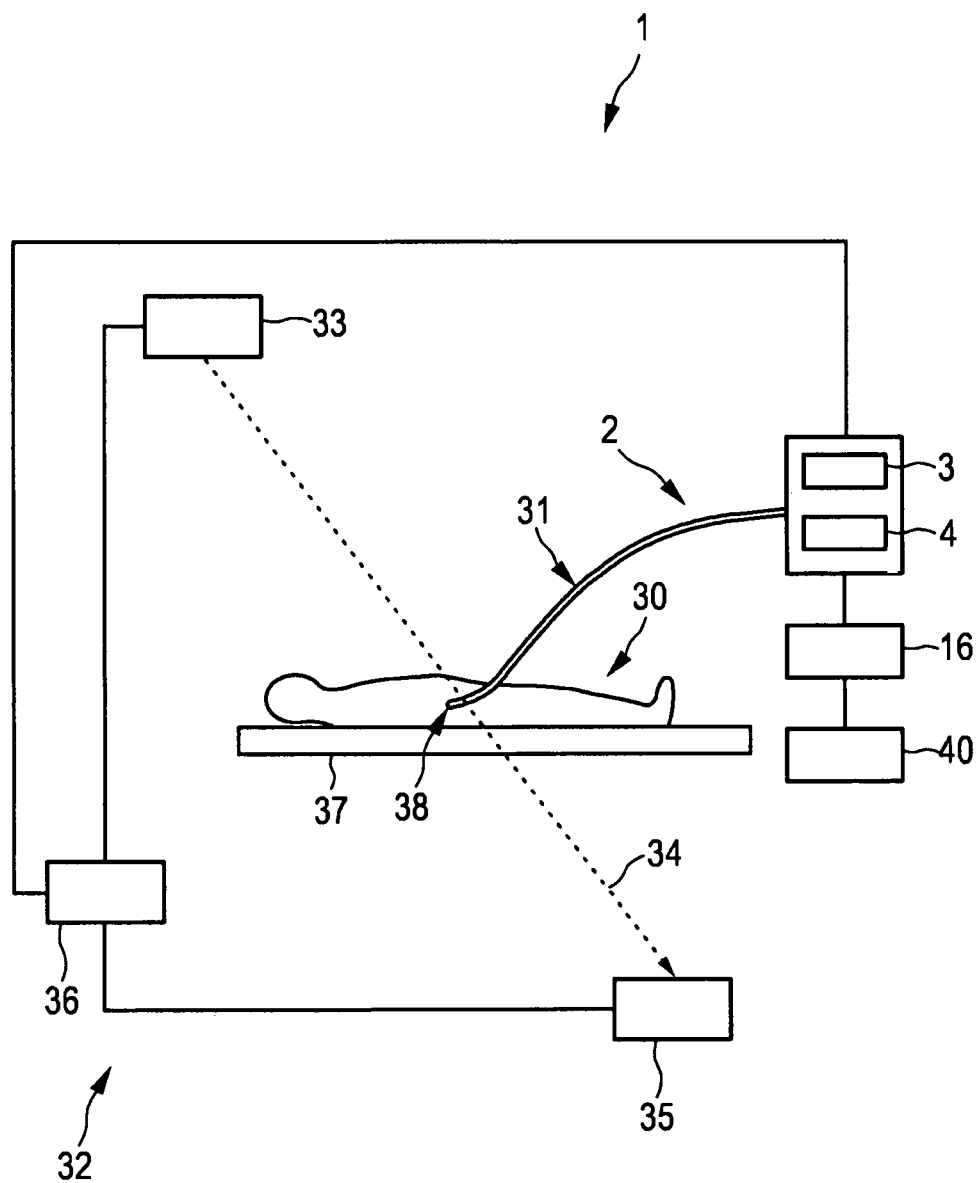
FIG. 1 shows schematically and exemplarily an embodiment of an apparatus for determining a property of a tissue.
Figure 2:
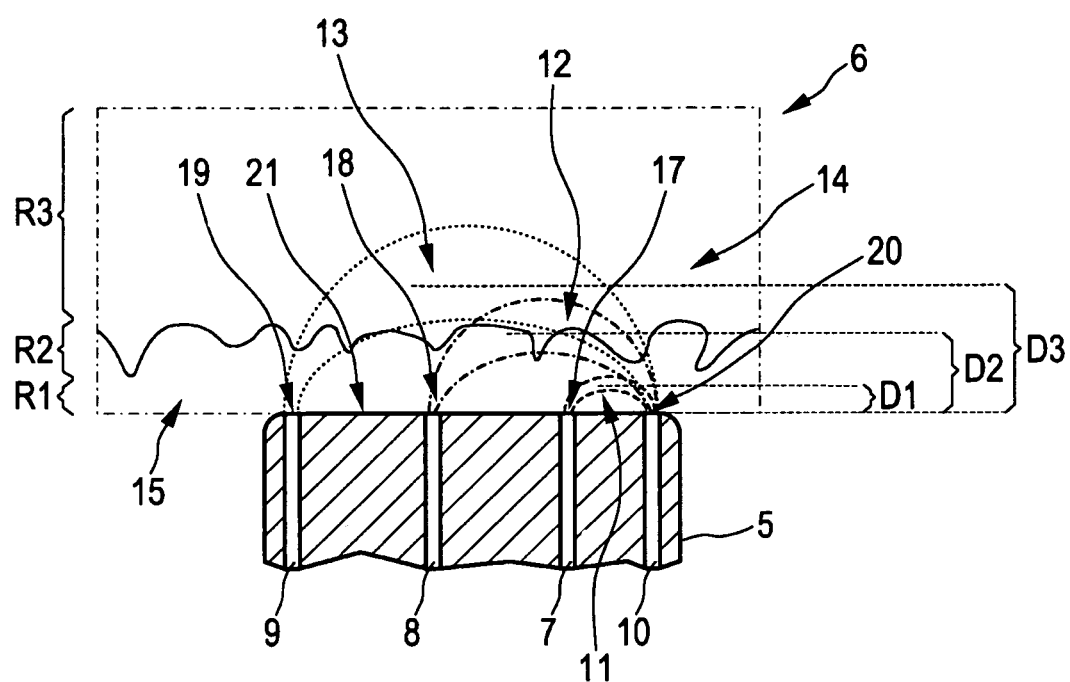
FIG. 2 shows schematically and exemplarily an embodiment of a measurement head of the apparatus.

FIG. 1 shows schematically and exemplarily an embodiment of an apparatus for determining a property of a tissue. In this embodiment the apparatus 1 is adapted to determine a property of cervical tissue. The apparatus 1 comprises an optical measurement device 2 with a light emission unit 3 including one or several light sources, a light detector 4 and optical fibers for guiding light generated by the light source 3 to the tissue and for guiding light from the tissue to the light detector 4. The optical fibers are arranged within a measuring probe 31 which is adapted to be introduced into a woman 30 lying on a table 37 for forwarding a tip 38 of the measuring probe 31 to the cervical. The tip 38 of the measuring probe 31 is exemplarily and schematically shown in more detail in FIG. 2.

The tip 38 of the measuring probe 31 comprises a measurement head 5 in which ends of optical fibers 7, 8, 9 for guiding light from the light emission unit 3 to the tissue 6 and an end of an optical fiber 10 for guiding light from the tissue 6 to the light detector 4 are arranged. The optical fibers 7, 8, 9 for guiding light to the tissue 6 can be regarded as being source fibers and the optical fiber 10 for guiding light from the tissue 6 to the light detector 4 can be regarded as being a detection fiber. The light emission unit 3 together with the source fibers 7, 8, 9 forms a light providing unit and the light detector 4 together with the detection fiber 10 forms a light detection unit.

The light providing unit and the light detection unit are adapted to generate a first signal being indicative of light 11 having been influenced by an epithelium region R1 of the tissue 6 comprising the epithelium 15 of the tissue 6, a second signal being indicative of light 12 having been influenced by a boundary region R2 of the tissue 6 comprising a boundary between the epithelium 15 and the stroma 14 of the tissue 6 and a third signal being indicative of light 13 having been influenced by a stroma region R3 of the tissue 6 comprising the stroma 14. In particular, the light providing unit and the light detection unit are adapted such that the generated first signal is indicative of light 11 having an average penetration depth D1 in the tissue 6 being smaller than 0.5 mm, the generated second signal is indicative of light 12 having an average penetration depth D2 in the tissue 6 being larger than 0.2 mm and smaller than 0.75 mm and the generated third signal is indicative of light 13 having an average penetration depth D3 in the tissue 6 being larger than 0.5 mm.

The light providing unit is adapted to provide several illumination locations 17, 18, 19 from which several light beams 11, 12, 13 emanate in an illumination direction, wherein the light detection unit is adapted to provide a detection location 20 at which the light is detected. In this embodiment the light providing unit and the light detection unit are adapted to provide three combinations 17, 20; 18, 20; 19, 20 of an illumination location and a detection location and to generate the first signal depending on the light beam 11 emanating from the illumination location and being detected by the detection location of a first combination 17, 20, the second signal depending on the light beam 12 emanating from an illumination location and being detected by a detection location of a second combination 18, 20 and the third signal depending on the light beam 13 emanating from an illumination location and being detected by a detection location of a third combination 19, 20.

The measurement head 5 comprises an outer plane abutting surface 21 for being abutted to the tissue 6, while illuminating the tissue 6 with light and detecting light from the tissue 6. In this embodiment the illumination and detection directions are perpendicular to the abutting surface 21, wherein the distance between the illumination location and the detection location of the first combination 17, 20 is smaller than 0.6 mm, in particular 0.3 mm, the distance between the illumination location and the detection location of the second combination 18, 20 is between 0.6 mm and 1.2 mm, in particular 1.0 mm, and the distance between the illumination location and the detection location of the third combination 19, 20 is between 1.2 mm and 3.0 mm, in particular 1.5 mm. The illumination and detection directions are preferentially defined by the orientation of the end faces of the source and detection fibers, respectively, i.e. since in this embodiment the illumination and detection directions are perpendicular to the outer plane abutting surface 21, the end faces of the source and detection fibers are preferentially parallel to the outer plane abutting surface 21.

The light emission unit 3 comprises three light sources, which can be operated sequentially, for coupling the light sequentially into the source fibers 7, 8, 9 such that the tissue 6 is illuminated only from a single illumination location at a time, in order to distinguish light emanating from different illumination locations 17, 18, 19 and being detected at the same detection location 20. In other embodiments also other techniques can be used for distinguishing the light emanating from the different illumination locations 17, 18, 19.

The light provided by the light source 3 is preferentially white light for performing a diffuse reflectance spectrometry measurement. However, the light emission unit can also be adapted to provide light within a desired wavelength range. The light detector comprises preferentially a spectrometer such that the first, second and third signals are preferentially spectra. In this embodiment the spectra are diffuse reflectance spectra. In another embodiment the light providing unit and the light detection unit can also be adapted to provide other spectra like fluorescence spectra or Raman spectra.

A position detection system 32 can be used to detect the position of the tip 38 of the measuring probe 31 within the person 30. In this embodiment the position detection system is an x-ray fluoroscopy system, in particular, an x-ray C-arm system. The x-ray fluoroscopy system comprises an x-ray source 33 for generating x-rays 34 which traverse the woman 30 on the table 37, wherein the x-rays 34, which have traversed the woman 30, are detected by an x-ray detector 35. The x-ray fluoroscopy system 32 further comprises a fluoroscopy control unit 36 for controlling the x-ray source 33 and the x-ray detector 35. The x-ray detector 35 generates x-ray images of the woman 30, which can be shown on a display 40. On the generated x-ray images the tip 38 of the measuring probe 31 is visible within the woman 30 such that the x-ray images show the position of the tip 38 of the measuring probe 31 within the woman 30.

The apparatus 1 further comprises a tissue property determination device 16 for determining a tissue property based on the first, second and third signals. The tissue property determination device 16 can be adapted to perform at least one of a feature extraction technique, a fitting to an analytical model and a multivariate analysis technique for determining the tissue property. These techniques can be used to directly determine the tissue property or to firstly determine an intermediate property, which can then be used for determining a final, desired tissue property. In particular, the tissue property determination device 16 can be adapted to perform the feature extraction techniques disclosed in the articles "Estimation of lipid and water concentrations in scattering media with diffuse optical spectroscopy from 900 to 1600 nm" by R. Nachabé et al., Journal of Biomedical Optics, volume 15, number 3 (2010) and "Optical Detection of the Brachial Plexus for Peripheral Nerve Blocks" by M. Brynolf et al., Regional Anesthesia and Pain Medicine, volume 36, number 4, pages 350 to 357 (2011), which are herewith incorporated by reference. Moreover, the tissue property determination device 16 can be adapted to perform a multivariate analysis technique in accordance with the technique disclosed in the article "Model based and empirical spectral analysis for the diagnosis of breast cancer" by C. Zhu et al., Optics Express, volume 16, number 19, pages 14961 to 14978 (2008), which is also herewith incorporated by reference.

If the tissue property determination device 16 firstly determines an intermediate property based on at least one of the above mentioned techniques, which is then used for determining the final tissue property, the intermediate property is at least one of blood fraction, blood saturation, water content, lipid content, beta carotene concentration, elastin concentration, NADH concentration, FAD concentration, porphyrin concentration and vitamin, in particular vitamin A, concentration. For each region, i.e. for the epithelium region, the boundary region and the stroma region, at least one intermediate property can be determined, wherein the final property can be determined based on the intermediate properties determined for the different regions.

The final tissue property determined by the tissue property determination device 16 can be, for instance, whether the tissue is healthy tissue or cancerous tissue. In particular, the tissue property determination device 16 can be adapted to determine a stage of cancer as the tissue property, in particular it can be determined whether invasive cancer is present. Moreover, the tissue property determination device 16 can be adapted to determine CIN as the tissue property. Thus, the tissue property determination device 16 can be adapted to distinguish between healthy tissue, CIN and cancer, in particular invasive cancer, wherein the tissue property determination device may also be adapted to discriminate between different grades of CIN, for instance, between CIN1, CIN2 and CIN3. The tissue property determination device 16 can also be adapted to discriminate between squamous and columnar healthy tissue, i.e. ectocervix and endocervix. Moreover, the tissue property determination device can be adapted to recognize non-cancerous pathological tissue, in particular different kinds of non-cancerous pathological tissue like inflammations or ulcers.

For determining the final tissue property based on one or several intermediate tissue properties the tissue property determination device 16 can comprise rules defining a final tissue property depending on one or several intermediate tissue properties. These rules can be predefined based on tissue samples having known intermediate tissue properties and known final tissue properties, wherein the rules can be predefined such that given the known intermediate tissue properties the rules lead to the known final tissue properties. For instance, the rules can define that, for instance, if a normalized blood fraction in the boundary region is larger than a predefined threshold and if the normalized blood fraction is smaller than the predefined threshold in the epithelium region and in the stroma region, CIN1 is present. Moreover, the rules can define that, if the normalized blood fraction is increased in the epithelium region, the boundary region and the stroma region, i.e. larger than predefined thresholds, invasive cancer is present. Also for other intermediate tissue properties and final tissue properties corresponding rules can be defined. The tissue property determination device 16 can also comprise rules for determining an intermediate tissue property or a final tissue property directly from the first, second and third signals, in particular from the corresponding spectra represented by the signals.

In an embodiment the tissue property determination device is adapted to apply the rules on values of the spectra at certain wavelengths, in order to determine intermediate or final tissue properties. For example, the rules can be applied to ratios of values of different spectra at the same certain wavelength and/or to ratios of values of the same spectrum at different certain wavelengths. The rules can also be defined such that they can be applied to a combination of these ratios. The certain wavelengths can indicate, for example, peaks or isobestic points of the respective spectrum. The rules can be predefined by calibration measurements, wherein the rules are predefined such that, if the rules are applied to training spectra of tissue having a known property, the rules lead to this known property.

The tissue property determination device 16 is further adapted to compare the signals with predefined expectations and to generate an error signal, if the signals do not correspond to the predefined expectations. For instance, the tissue property determination device 16 can be adapted to directly compare the signals, i.e. the optical measurements, with the expectations, or the property determination unit can be adapted to process the signals and to compare the processing results with the expectations. The processing can be defined by processing steps, which are performed for determining the tissue property. Thus, if the measurements or the analysis are yielding wrong or inclusive results, an error signal can be generated. This error signal can be an acoustical and/or optical signal, which can be output, in order to indicate the error to a user. The error signal can also be indicative of the kind of error, wherein the kind of error can be shown to the user on the display 40. Moreover, the apparatus can be adapted to repeat the measurement and the analysis, if an error signal has been generated.

For instance, the tissue property determination device can be adapted to generate an error signal, if a signal, in particular a value of a spectral signal at a certain wavelength, provided by the optical measurement device is larger or smaller than a maximally or minimally, respectively, expected signal. If a signal provided by the optical measurement device is smaller than a minimally expected signal, this may indicate that the measurement head is not in contact with the tissue or that something in the optical measurement device is broken. The tissue property determination device can also be adapted to generate an error signal, if an intermediate property is larger than a maximally expected intermediate property or smaller than a minimally expected intermediate property. For instance, if as an intermediate property the blood fraction has been determined and if the blood fraction is larger than a maximally expected blood fraction, an error signal can be generated, wherein in this case the error signal may indicate that the tissue is bleeding at the monitored position. The tissue property determination device can of course also be adapted to compare the signals directly, to compare the intermediate properties and/or to compare the final properties with other predefined expectations and to generate an error signal, if the predefined expectations are not met.

Figure 3:
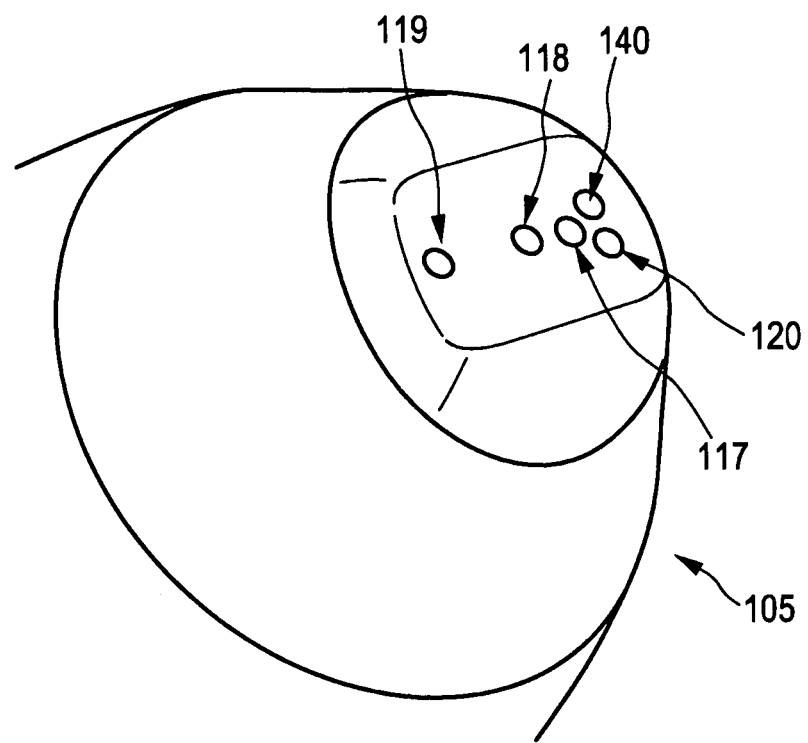
FIG. 3 shows schematically and exemplarily a further embodiment of the measurement head of the apparatus.

In an embodiment the light detection unit can be adapted to provide a further detection location as schematically and exemplarily shown in FIG. 3.

FIG. 3 shows schematically and exemplarily a further embodiment of a measurement head 105 comprising three illumination locations 117, 118, 119 formed by ends of corresponding source fibers and two detection locations 120, 140 formed by ends of corresponding two detection fibers. In this embodiment two first signals can be generated by using the two combinations of the first illumination location 117 and the detection locations 120, 140, two second signals can be generated by using the two combinations of the second illumination location 118 and the detection locations 120, 140 and two third signals can be generated by using the two combinations of the third illumination location 119 and the detection locations 120, 140. In this embodiment the light detector 4 comprises preferentially two spectrometers, wherein the light detected at the first detection location 120 is preferentially guided to a first spectrometer and the light detected at the second detection location 140 is preferentially guided to a second spectrometer. The first spectrometer is preferentially a visible light spectrometer and the second spectrometer is preferentially an infrared light spectrometer.

The measurement head 105 shown in FIG. 3 can be used with the apparatus described above with reference to FIGS. 1 and 2, wherein instead of the measurement head 5 exemplarily and schematically shown in FIG. 2 the measurement head 105 schematically and exemplarily shown in FIG. 3 and wherein a light detector having two spectrometers can be used. This apparatus allows generating two sets of signals which correspond to a visible wavelength range and an infrared wavelength range. The tissue property determination device 16 is then preferentially adapted to determine the tissue property based on the two sets of signals. For instance, the first signals can together be used for determining an intermediate tissue property of the epithelium region, the second signals can together be used for determining an intermediate tissue property of the boundary region and the third signals can together be used for determining an intermediate property of the stroma region, wherein these intermediate tissue properties can be used by the tissue property determination device 16 for determining a final tissue property, in particular to determine whether the tissue is healthy tissue or cancerous tissue.

Figure 4:
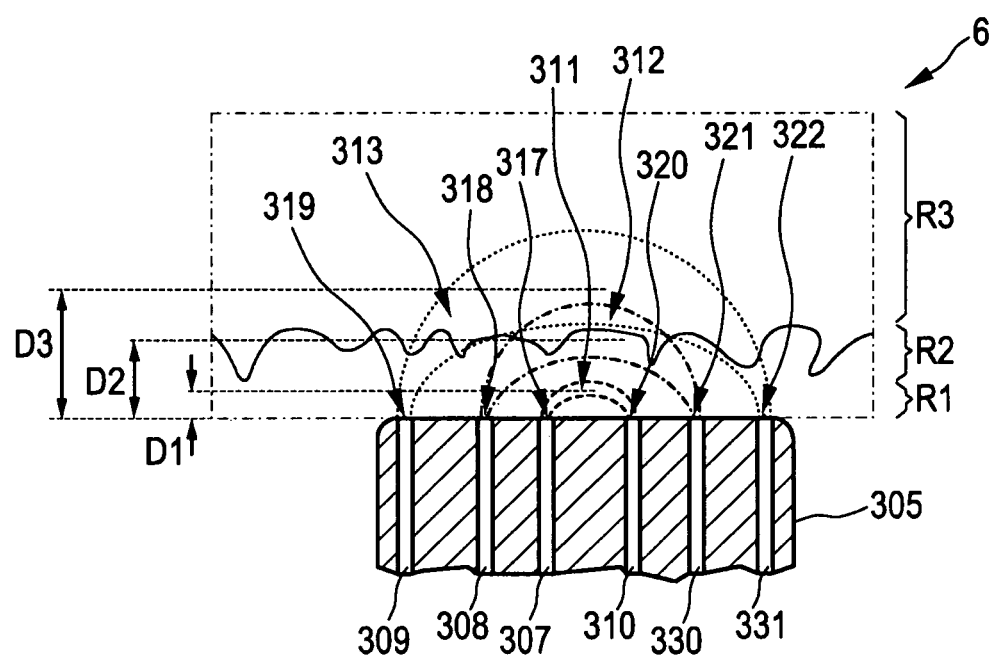
FIG. 4 shows schematically and exemplarily a further embodiment of the measurement head of the apparatus.

FIG. 4 shows schematically and exemplarily a further embodiment of a measurement head 305. The measurement head 305 comprises three source fibers 307, 308, 309 and three detection fibers 310, 330, 331. The source fibers and the detection fibers form three combinations, a first combination defined by the source fiber 307 and the detection fiber 310, a second combination defined by the source fiber 308 and the detection fiber 330 and a third combination defined by the source fiber 309 and the detection fiber 331. The first signal is generated from the light 311 defined by the first combination, the second signal is generated from the light 312 defined by the second combination and the third signal is generated from the light 313 defined by the third combination. The source fibers 307, 308, 309 define illumination locations 317, 318, 319, from which the light emanates, and the detection fibers 310, 330, 331 form detection locations 320, 321, 322, at which the light is detected, wherein in this embodiment to each illumination location a single detection location is assigned. The light detector is preferentially adapted to determine for each detection location, i.e. for each of the three combinations of source fiber and detection fiber and, thus, of illumination location and detection location, a spectrum, wherein the resulting three spectra can be used by the tissue property determination device 16 for determining the tissue property.

The measurement head 305 shown in FIG. 4 can be used with the apparatus described above with reference to FIGS. 1 and 2, wherein instead of the measurement head 5 exemplarily and schematically shown in FIG. 2 the measurement head 305 schematically and exemplarily shown in FIG. 4 can be used.

Figure 5:
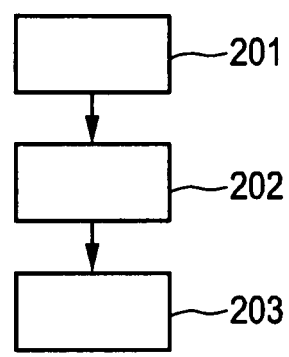
FIG. 5 shows a flowchart exemplarily illustrating an embodiment of a method for determining a property of a tissue.

In the following an embodiment of a method for determining a property of a tissue will exemplarily be described with reference to a flowchart shown in FIG. 5.

In step 201 light for illuminating the tissue is provided by a light providing unit of an optical measurement device and light from the tissue is detected by a light detection unit of the optical measurement device, wherein the light providing unit and the light detection unit generate a first signal being indicative of light having been influenced by an epithelium region of the tissue comprising the epithelium, a second signal being indicative of light having been influenced by a boundary region of the tissue comprising a boundary between the epithelium and the stroma and a third signal being indicative of light having been influenced by a stroma region of the tissue comprising the stroma. In step 202 a tissue property, for instance, whether the tissue is healthy tissue or cancerous tissue, is determined based on the first, second and third signals by a tissue property determination device. In step 203 the determined tissue property is shown on a display to a user.

The apparatuses described above with reference to FIGS. 1 to 4 can be adapted to allow even less experienced health workers to reliably diagnose and stage cancer.

Invasive squamous cell cervical cancers, which account for more than 98 percent of cervical cancer cases in developing countries, are preceded by a long phase of pre-invasive disease, collectively referred to as CIN. CIN typically arises from the lower parts of the epithelium. It can be categorized into grades 1, 2 and 3 (CIN1, CIN2, CIN3) depending upon the proportion of the thickness of the epithelium showing differentiated cells. CIN2 and CIN3 are the optimal stages for treatment. CIN1 is usually not treated in developed countries, but kept under observation. It is often treated in developing countries however, when follow-up is an issue.

Once the cancer reaches an invasive stage, in particular into the stroma, immediate, intensive treatment is needed. Therefore it is important to distinguish invasive cancer from non-invasive cancer-in-situ, because the treatment options are radically different. CIN and in-situ cancer can be treated by local excision, while invasive cancer will usually require full hysterectomy, i.e. the complete removal of the cervix and the uterus, even though very early invasive stages so called micro-invasive cancer or stage 1A can still be treated successfully by local excision if conservation of fertility is desired. It is also important to distinguish CIN from healthy tissue and, to a lesser degree, to distinguish the different levels of CIN.

In the prior art on suspicion of cervical cancer a first diagnosis and staging is usually done by colposcopy. Unfortunately, colposcopy requires a very experienced operator and shows strong observer-to-observer variations. It can also only observe the surface of the cancer, meaning it cannot distinguish invasive from non-invasive cancer. For this reason, often a punch biopsy may be required. However, biopsies take time, typically days. In rural areas of developing countries, where women often have to travel far to see a gynecologist, this waiting time represents a considerable loss in income, especially since these women generally travel with a male relative. Any waiting time will add to a loss in follow-up, so the biopsy is frequently skipped. Also biopsies can only be taken at a few suspicious looking points at the cervix. That leaves the risk that an invasive cancer is not recognized, because the biopsy locations only exhibit pre-invasive cancer. Alternatively, a full hysterectomy may be done, even though the invasive portion may be limited to a very small, in particular micro-invasive, lesion, which could have been removed by conisation. Last but not least, a colposcope or a typical visual inspection can only survey the outer portion of the cervix, i.e. the ectocervix. Cancerous lesions deeper in the opening of the cervix, the so called endocervix, will generally remain undetected.

In contrast, the apparatus described above with reference to FIGS. 1 to 4 provides a photonic tool that can reliably detect and stage cervical cancer in real-time, which can be an important complement or even an alternative to colposcopy and biopsy, in order to improve the outcome of countless of cervical cancer cases.

The apparatus provides a photonic-tools-based probe designed to detect and stage cervical cancer in the ecto- and endocervix. Photonic tools send light from a probe, i.e. the measurement head, into biological tissue being in this embodiment the cervix and detect light returned from the tissue, wherein the returned light is analyzed. Light generation and analysis can be done in an optical console and transported to and from the probe by optical fibers. Optical fibers which transport light from the console to the probe are called source fibers, while fibers that transport light from the probe to the console are called collection fibers or detection fibers. Visible and near infrared light can penetrate up to a few mm into biological tissue. By changing the geometry of the probe, for instance, the distance and/or the angle of the source and collection fibers, it is possible to determine how deep the light that is analyzed has penetrated into the tissue on average.

The probe is preferentially a non-penetrating probe which is in contact with the cervix during measurement. The probe preferentially comprises different combinations of source and detector fibers so that the light for each source-detector combination will on average probe a different depth into the same tissue location. In an embodiment one source-detector combination substantially probes the epithelium with an average penetration depth smaller than 0.5 mm, one source-detector combination substantially probes the boundary region between epithelium and stroma with an average penetration depth in the range between 0.2 mm and 0.75 mm, and one source-detector combination substantially probes the stroma/muscle region with an average penetration depth larger than 0.5 mm. Preferentially depending on the differences in the spectra between the three source-detector combinations the apparatus will discriminate between healthy tissue, CIN and invasive cancer and display the result to the operator.

It is further preferred that the apparatus provides a finer discrimination, for instance, between CIN1 and CIN2, and between stage 1A and stage 1B invasive cancer. Alternatively or in addition, the apparatus may discriminate between squamous and columnar healthy tissue, in particular between ectocervix and endocervix healthy tissue, and recognize typical non-cancerous pathological tissue like inflammations or ulcers.

In an embodiment the different spectra can be processed, for instance, subtracted from each other, divided by each other, integrated, differentiated, scaled, et cetera, wherein the resulting one or several processed spectra can be used for determining intermediate properties or final properties based on predefined rules to be applied to the one or several processed spectra.

The apparatus comprises preferentially a probe head, i.e. a measurement head, which sends light into the tissue, wherein some of the light will be send back to the probe head and detected. If the source of the light and the detector are both small, for instance, if they are formed by faces of optical fibers, the light that is detected will typically have passed through a banana-shaped volume of the tissue. The volume and depth probed will depend on the exact nature and geometry of both the light provision and the light detection. Preferentially three source-detector combinations are used, which probe different depths of the same tissue location. These depths are chosen such that the epithelium, the boundary region between epithelium and stroma, and the stroma are each probed.

Although the apparatus is preferentially adapted for the detection and staging of cervical cancer, the apparatus can also be adapted to determine another tissue property, in particular of another part of a person or of an animal. For instance, the apparatus may be adapted for the detection of other types of cancer that arise from squamous epithelia like oral cancer.

Although in the above described embodiments the apparatus uses optical fibers to transport light from a source and to a detector, alternatively or in addition the measurement head may comprise light sources like light emitting diodes and/or photodetectors for illuminating the tissue and for receiving light from the tissue, in particular without using optical fibers.

Although in the above described embodiments diffuse reflectance spectra are preferentially measured, wherein the tissue is illuminated with white light, the apparatus can also be adapted to measure fluorescence spectra or Raman scattering spectra, for example, as described in the article "An Investigation of Fiber-Optic Probe Designs for Optical Spectroscopic Diagnosis of Epithelial Pre-Cancers", by M. Skala et al, Lasers in Surgery and Medicine, volume 34, number 1, pages 25 to 38 (2004), which is herewith incorporated by reference. The apparatus can also be adapted to measure a combination of diffuse reflectance, fluorescence and/or Raman scattering spectra.

The apparatus preferentially comprises a flat probe head, i.e. a measurement head, which comprises one detection fiber and three source fibers, leading to three different source-detector combinations. The fibers preferentially end in a straight face, parallel to the edge of the probe. The probe head can slide along the edge of the cervix, but will not penetrate. The source fibers are at different distances from the detector fibers. In such a configuration the light that is detected will on average have penetrated about one half of the distance between the fibers into the tissue. Therefore if the distance between the source fibers and the detection fibers is 1.5 mm, 1 mm and 0.3 mm, the average measurement depth will be approximately 0.75 mm, 0.5 mm and 0.15 mm respectively, so that the epithelium, the boundary between epithelium and the stroma are all substantially probed separately, wherein it is assumed that the depth on the stroma is about 0.2 mm to 0.5 mm with strong spatial variations, i.e. wherein it is assumed that the boundary between the stroma and the epithelium lies between 0.2 mm and 0.5 mm below the surface of the tissue.

The tissue property determination device can be adapted to perform a feature extraction technique, a fitting technique for fitting an analytical model and/or a multivariate analysis technique. If the multivariate analysis technique is applied, by using a suitable training set characteristic patterns in the three spectra for different tissue properties like different types of tissues and different stages of cancer will automatically be recognized. If the feature extraction technique or the fitting to an analytical model is used, preferentially firstly each region, in particular each spectrum, is analyzed individually. For example, a measure of the blood fraction of the tissue may be extracted from the diffuse reflectance spectrum by either method, in order to determine for each region, in particular for each spectrum, a blood percentage value. Thus, preferentially three blood percentage values are obtained for the three regions. These values are typically different for the epithelium, the boundary region and the stroma, even for healthy tissue. The tissue property determination device therefore preferentially normalizes the values. Higher than normal blood fractions are one sign of cancerous cells. So for a CIN1 lesion, a higher blood fraction is expected in the boundary region, but not or too a lower degree in the stroma or in the epithelium. An invasive stroma on the other hand would show increased blood fraction in all three spectra. Similar patterns can be determined for the other lesion types and for other biomarkers. Typical biomarkers, which can be determined by using photonic tools, are blood fraction, blood saturation, water content, lipid content, beta carotene concentration, and light scattering from diffuse reflectance spectra and elastin, collagen, NADH, FAD, porphyrin and vitamin A concentrations from fluorescence spectra. Typical signs of cancer are increased blood fraction, increased scattering, increased NADH, increased FAD and decreased blood oxygenation.

Although in the above described embodiments the distances between an illumination location and a detection location of different combinations are different, in order to generate different signals which correspond to different penetration depths, in other embodiments alternatively or in addition the illumination and detection directions, in particular, the angles of the illumination fibers and the detection fibers can be varied, in order to provide different penetration depths. Also optical elements like lenses can be arranged in front of one or several fibers for modifying the penetration depth.

The light used for illuminating the tissue for generating the different signals can be within the same wavelength range, in particular, it can be white light. Moreover, the light used for illuminating the tissue for generating the different signals can be within different wavelength ranges such that the illumination light used for generating a certain signal is within a certain wavelength range that is different to another wavelength range used for generating another signal.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The determination of the tissue property based on the signals and/or the control of the apparatus for determining a property of a tissue based on the method for determining a property of a tissue can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an apparatus for determining a property of a tissue, particularly cancer of cervical tissue. A light providing unit provides light for illuminating the tissue and a light detection unit detects light from the tissue, wherein a first signal being indicative of light having been influenced by an epithelium region, a second signal being indicative of light having been influenced by a boundary region and a third signal being indicative of light having been influenced by a stroma region are generated, and wherein a tissue property is determined based on the first, second and third signals. This allows for an determination of a tissue property, which is based on a combination of optical properties measured in the three different regions, resulting in an improved determination of the tissue property, in particular in improved cancer detection.

The invention claimed is:

1. An apparatus for determining a property of a tissue of a subject, the tissue comprising epithelium and stroma, the apparatus comprising:
an optical measurement device including a light source for providing light for illuminating the tissue from a plurality of illumination locations at a surface of the subject, and a light detector for detecting light from the illuminated tissue through a plurality of detection locations, the light detector configured to use a different spectrum for each of the detection locations, wherein the light source and the light detector are configured to: (i) generate a plurality of first signals being indicative of light provided at a first illumination location and having been influenced by an epithelium region of the tissue comprising the epithelium, a plurality of second signals being indicative of light provided at a second illumination location and having been influenced by a boundary region of the tissue comprising a boundary between the epithelium and the stroma, and a plurality of third signals being indicative of light provided at a third illumination location and having been influenced by a stroma region of the tissue comprising the stroma, and (ii) determine (a) a first set of signals comprising one of each of the first, second, and third signals in a first wavelength range of a first of the detection locations, and (b) a second set of signals comprising one of each of the first, second, and third signals in a second wavelength range of a second of the detection locations, wherein the first, second and third illumination locations are different distances from the detection locations, enabling light penetration to different depths, respectively; and
a computer configured to execute program code causing the computer to determine a tissue property of the tissue based on the first set of signals in the first wavelength range and the second set of signals in the second wavelength range, wherein the tissue property is at least one of healthy tissue, cervical intraepithelial neoplasia and cancer,
wherein average penetration depths into the tissue of the light provided at the first, second and third illumination locations are determined, at least in part, by distances of the first, second and third illumination locations from a given one of the detection locations, respectively.

2. The apparatus as defined in claim 1, wherein the light source and the light detector are configured such that:
each of the generated first signals is indicative of light having the average penetration depth in the tissue being smaller than 0.5 mm,
each of the generated second signals is indicative of light having the average penetration depth in the tissue being larger than 0.2 mm and smaller than 0.75 mm, and
each of the generated third signals is indicative of light having the average penetration depth in the tissue being larger than 0.5 mm.

3. The apparatus as defined in claim 1, wherein the generated first, second and third signals are first, second and third spectra, respectively, and wherein the program code further causes the computer to determine the tissue property based on the first spectrum, second spectrum and the third spectrum.

4. The apparatus as defined in claim 1, wherein the optical measurement device is configured to:
generate additional first signals being indicative of light having been influenced by the epithelium region, wherein different first signals are indicative of light within different wavelength ranges,
generate additional second signals being indicative of light having been influenced by the boundary region, wherein different second signals are indicative of light within different wavelength ranges, and
generate additional third signals being indicative of light having been influenced by the stroma region, wherein different third signals are indicative of light within different wavelength ranges,
wherein the program code further causes the computer to determine the tissue property based on the additional first, second and third signals, as well as the first, second and third signals.

5. The apparatus as defined in claim 1, wherein the optical measurement device further includes a measurement head with an outer plane abutting surface for being abutted to the tissue, while illuminating the tissue with light and detecting light from the illuminated tissue,
wherein the illumination and detection directions are perpendicular to the abutting surface, and
wherein a distance between the first illumination location and each of the detection locations is smaller than about 0.6 mm, a distance between the second illumination location and each of the detection locations is between about 0.6 mm and about 1.2 mm and a distance between the third illumination location and each of the detection locations is between about 1.2 mm and about 3.0 mm.

6. The apparatus as defined in claim 1, wherein the program code further causes the computer to perform at least one of a feature extraction technique, a fitting to an analytical model, and a multivariate analysis technique for determining the tissue property.

7. The apparatus as defined in claim 1, wherein the program code further causes the computer to:
determine as an intermediate property at least one of blood fraction, blood saturation, water content, lipid content, carotene concentration, elastin concentration, collagen concentration, nicotinamide adenine dinucleotide concentration, flavin adenine dinucleotide concentration, porphyrin concentration, vitamin concentration in at least one of the epithelium region, the boundary region and the stroma region, and
determine the tissue property depending on the determined intermediate property.

8. The apparatus as defined in claim 1, wherein the program code further causes the computer to compare the signals with predefined expectations, and generates an error signal when the signals do not correspond to the predefined expectations.

9. The apparatus of claim 1, wherein the plurality of locations correspond to optical fibers for guiding light to the tissue.

10. The apparatus of claim 9, wherein the light detector comprises a detection optical fiber.

11. The apparatus of claim 1, wherein the first wavelength range is a visible wavelength range and the second wavelength range is an infrared wavelength range.

12. A method for determining a property of a tissue of a subject comprising epithelium and stroma, the method comprising:
- causing a light to illuminate the tissue with light from a plurality of illumination locations at a surface of the subject, the light from the illuminated tissue being detected in response to the light from the plurality of illumination locations, respectively;
- receiving (i) a plurality of first signals indicative of detected light provided in response to light from a first illumination location and having been influenced by an epithelium region of the tissue comprising the epithelium, (ii) a plurality of second signals being indicative of detected light provided in response to light from a second illumination location and having been influenced by a boundary region of the tissue comprising a boundary between the epithelium and the stroma, and (iii) a plurality of third signals being indicative of detected light provided in response to light from a third illumination location and having been influenced by a stroma region of the tissue comprising the stroma, wherein the first, second and third illumination locations are different distances from each of a plurality of detection locations processed at different spectra, enabling light penetration to different depths, respectively;
- determining (a) a first set of signals comprising one of each of the first, second, and third signals in a first wavelength range of a first of the detection locations, and (b) a second set of signals comprising one of each of the first, second, and third signals in a second wavelength range of a second of the detection locations; and
- determining a tissue property based on the determined first set of signals in the first wavelength range and the determined second set of signals in the second wavelength range, wherein the tissue property is at least one of healthy tissue, cervical intraepithelial neoplasia and cancer.

13. A non-transitory computer readable medium, having embodied thereon a computer program for determining a property of a tissue, the tissue comprising epithelium and stroma, the computer program, when executed by a computer, causing the computer to perform the method as defined in claim 12.

14. The method of claim 12, wherein the light from each of the plurality of illumination locations is provided perpendicular to an abutting surface of a measurement head, including the plurality of illumination locations, the abutting surface abutting the surface of the subject.

15. The method of claim 12, wherein the first wavelength range is a visible wavelength range and the second wavelength range is an infrared wavelength range.

* * * * *